United States Patent
Obenchain et al.

(10) Patent No.: US 6,869,398 B2
(45) Date of Patent: Mar. 22, 2005

(54) FOUR-BLADE SURGICAL SPECULUM

(76) Inventors: Theodore G. Obenchain, 355 E. Grand Ave., Suite 2, Escondido, CA (US) 92025; Laurence M. McKinley, 355 E. Grand Ave., Suite 2, Escondido, CA (US) 92025

( * ) Notice: Subject to any disclaimer, the term of this patent is extended or adjusted under 35 U.S.C. 154(b) by 0 days.

(21) Appl. No.: 10/337,613

(22) Filed: Jan. 6, 2003

(65) Prior Publication Data

US 2004/0133077 A1 Jul. 8, 2004

(51) Int. Cl.[7] ................................................. A61B 1/32
(52) U.S. Cl. ...................... 600/224; 600/210; 600/214; 600/217; 600/219
(58) Field of Search ............................... 600/201, 210, 600/214, 217, 219, 224, 225, 226, 227

(56) References Cited

U.S. PATENT DOCUMENTS

| | | | | |
|---|---|---|---|---|
| 380,745 A | * | 4/1888 | Chamberlin | 600/224 |
| 761,821 A | * | 6/1904 | Clark et al. | 600/224 |
| 3,728,006 A | * | 4/1973 | Wilder et al. | 600/210 |
| 3,858,578 A | | 1/1975 | Milo | |
| 4,971,038 A | * | 11/1990 | Farley | 600/230 |
| 5,299,563 A | * | 4/1994 | Seton | 600/215 |
| 5,449,374 A | * | 9/1995 | Dunn et al. | 606/208 |
| 5,667,481 A | * | 9/1997 | Villalta et al. | 600/224 |
| 5,709,646 A | * | 1/1998 | Lange | 600/203 |
| 5,728,046 A | * | 3/1998 | Mayer et al. | 600/210 |
| 5,928,139 A | * | 7/1999 | Koros et al. | 600/205 |
| 5,931,777 A | * | 8/1999 | Sava | 600/213 |
| 5,993,385 A | | 11/1999 | Johnston et al. | |
| 6,159,167 A | * | 12/2000 | Hardin-Naser | 600/587 |
| 6,302,842 B1 | * | 10/2001 | Auerbach et al. | 600/220 |
| 6,572,541 B1 | * | 6/2003 | Petersvik | 600/233 |
| 2001/0012942 A1 | * | 8/2001 | Estes et al. | 606/105 |

* cited by examiner

Primary Examiner—Pedro Philogene
Assistant Examiner—David A Bonderer
(74) Attorney, Agent, or Firm—Christie, Parker & Hale, LLP

(57) ABSTRACT

A speculum system with four blades is provided. The blades project in approximately the same direction, and each blade is connected to a handle linearly or at an angle. The handles are coupled together. In one embodiment, the distance between the blades is changeable so that a field of view defined as the viewable area between the blades can be increased or decreased. In another embodiment, the blades include texture, such as ribs, holes or teeth to grip onto surrounding muscle fiber. In yet another embodiment, a stabilizing arm attaches to a stabilizing object, such as a table or heavy or immovable object, and to one of the handles to stabilize the speculum system.

21 Claims, 3 Drawing Sheets

FOUR-BLADE SURGICAL SPECULUM

FIELD OF THE INVENTION

The invention relates to a speculum system, more particularly a surgical speculum system.

BACKGROUND OF THE INVENTION

Medical professionals frequently employ specula to view or dilate areas within the body. Specula are well known. The first reference to a speculum occurred in 1597 and related to a device for dilating the eyelids. A century later, oral and vaginal specula were disclosed "wherewith the womb or mouth is dilated or opened." William A. Smellie describes in his 1752 treatise on midwifery a "speculum matricis" for spreading open the cervix to look into the womb. Nearly a century later, Robert Graves disclosed the Grave's speculum, a bivalve vaginal speculum that is still in use today. By 1862, a catalog produced at an international exhibit in Britain disclosed specula for dilating the eye, ear, vagina, rectum and nose.

These specula typically have smooth surfaces capable of slipping comfortably into and dilating a bodily orifice for viewing by a medical professional. The medical professional typically views the area of interest by looking down the center of the smooth, dilating surface, which is frequently constructed as bivalve blades, a hollow cone, or a cylinder. The inside surface of the specula are also typically highly reflective, so that light from a head light or ambient light in the room reflects off of the surface and illuminates the area of interest.

More recently, several specula useful in spinal surgery have been disclosed. The Cloward speculum, described in the 1950's, includes a rigid, hollow cylinder fixed to a perpendicular plane, or "foot". The foot has a cut-out on the overlapping area so the view down the center of the cylinder is unobstructed. The foot also includes metal prongs. These prongs can be hammered into a cervical vertebral body to stabilize the speculum. The surgeon can then drill near affected cervical discs and insert a dowel cut from the iliac crest to distract the disc space of the affected discs.

Parviz Kambin used a two-portal speculum system for spinal surgery, with a hole on both sides of a patient's spine. In this design, a speculum dilates each hole. A surgeon "works down" one hole with surgical instruments and looks down the second hole with, for example, an endoscope to view what he or she is doing. However, one of the disadvantages of this approach is that endoscopes do not accurately indicate depth, and surgeons frequently may damage the lens of the endoscope with the surgical instruments or could damage sensitive neurological tissue by feeling around the cavity with the instruments to determine "depth of field."

Another speculum used in spinal surgery is the Michelson speculum. It includes a rigid, hollow cylinder with teeth projecting outwardly from one end. The teeth are driven into the vertebrae adjacent to a distracted intervertebral space. The rigidity of this speculum can be a problem, however, as the size and shape of the dilation cannot be easily changed, if at all. Additionally, surgeons may use "cottonoids," small structures the size of postage stamps with strings attached, to control bleeding. These cottonoid strings may obstruct vision inside of the Michelson speculum and are easily dislodged or snared by the passage of instruments through a rigid speculum.

A standard posterior approach to the spine with these specula entails stripping the muscles off of the back of the spine, traumatizing the muscles. Stretching and tearing of the muscles can cause inflamation and extreme pain. Sometimes up to two or three days of IV narcotic pain medication are necessary to aid such post-surgical recovery. This traditional approach to the spine results in denervation of the paraspinous muscles, which may be the reason for some residual post-surgical back pain. When muscles are denervated, they do not function normally and the biomechanical stability of the spine can be damaged. The multifidus muscle, the large muscle in the center of the back, is made in layers and attached in layers to the inferior edge of the lamina. This muscle functions inside its cylindrical fascia as a stiffener and stabilizer, supporting axial loads, and helping to control rotational and torsional movement of the lumbar spine. Damage to the multifidus muscle thus greatly weakens the structural integrity of the back.

Another disadvantage with these specula is that the specula are not held rigidly in place, either because they are manually held in place or are secured by gripping into bone or other parts of a subjects' body. Because these specula are not held rigidly in place, the specula cannot be effectively used as a reference point in techniques like image guided surgery.

Accordingly, a need exists for a new, improved surgical speculum capable of assisting a surgeon in performing spinal surgery without the above-mentioned disadvantages.

SUMMARY OF THE INVENTION

The present invention is directed to a surgical speculum system. One embodiment includes four blades, each coupled to a handle. The term "blade" refers to any rigid material that is substantially long and thin. Each blade has an inner surface and an outer surface. In this embodiment, the inner surface of each blade faces the inner surface of one other blade, and the handles of the facing blades are coupled together.

In this embodiment, one of the handles also includes a coupler for removably coupling a handle of a non-facing blade, so that all of the blades can be coupled together, projecting in a substantially parallel direction. This arrangement of the blades allows a surgeon to dilate a surgical opening in four directions. The blades can extend from the handles linearly or at an angle, so a surgeon's field of vision down the center of the blades is not obstructed.

In another embodiment, the distance between the facing blades is changeable. By adjusting the distance between the facing blades, the surgeon is able to easily insert the speculum into a narrow surgical opening and then separate the facing blades to dilate that opening. Additionally, the surgeon can adjust the spacing between the different facing blades to most effectively illuminate or view an area of interest.

In several embodiments, the speculum system facilitates a surgical approach with smaller incisions. Such "minimally invasive surgery" can reduce tissue trauma and post operative pain for the patient, which will facilitate a quicker than normal recovery. Also, this type of surgery may be more cost-effective than traditional open surgical techniques, while permitting safe surgery because all of the relevant anatomical structures can be clearly seen.

BRIEF DESCRIPTION OF THE DRAWINGS

These and other features and advantages of the present invention will be better understood by reference to the following detailed description when considered in conjunction with the accompanying drawings where.

DETAILED DESCRIPTION OF THE DRAWINGS

Figure 1:
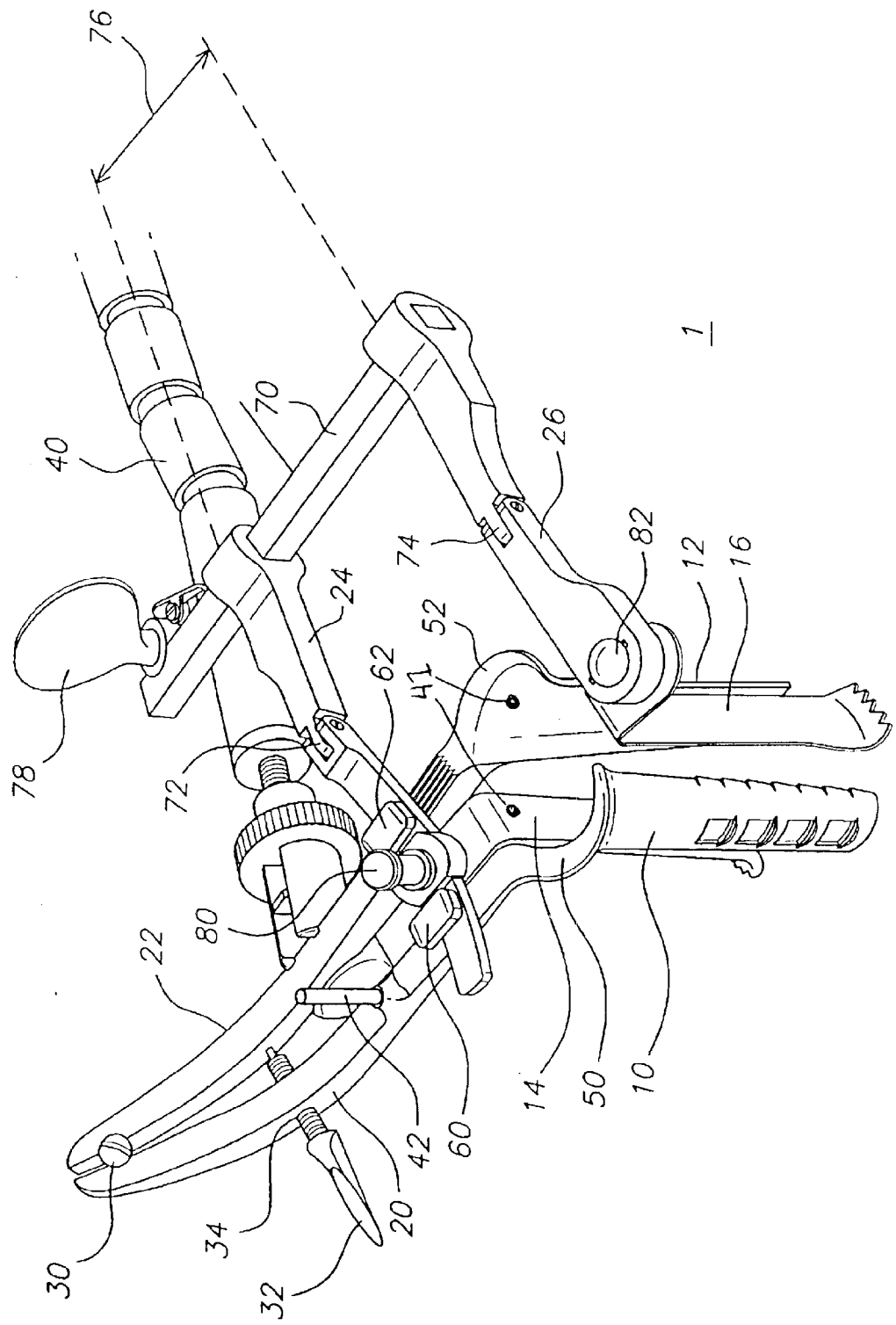
FIG. 1 is a side perspective view of one embodiment of an exemplary speculum system according to the invention.

FIG. 1 shows an embodiment of a speculum system 1 with four blades 10, 12, 14, 16 attached to four handles 20, 22, 24, 26. The first and second handles 20, 22 are attached by a hinge 30 and curve upward. It is also within the scope of this invention for the handles 20, 22 to be straight. Although the handles may be designed with a fixed distance therebetween, in this embodiment, a screw 32 is threaded through a hole 34 in the first handle 20 to push against the adjacent solid surface of the second handle 22. This screw 32 thereby sets a distance between the first and second handles 20, 22. Any other mechanism for distancing the first and second handles 20, 22, such as a latch, variable spacer, or the like can also be used.

Again, although not required in this embodiment, an optional stabilizing arm 40 grips the second handle 22 to stabilize the speculum system 1 to a fixed position. The stabilizing arm 40 may alternatively grip onto any other suitable portion of the speculum. The stabilizing arm 40 is attached at another end to a stabilizing object (not shown), such as a table or heavy or immovable object. Because the stabilizing arm can hold the blades rigidly in place, the blades can become an ideal reference point for image guided technology. The tops of the blades can be marked with "fiducials," 41 or little reflective balls or domes to give reference points in image guided surgery. This embodiment also includes an optional attachment post 42 protruding upward from the first handle 20 for attaching surgical tools and the like.

The first and second handles 20, 22 are molded to a first and second blade 10, 12, respectively. The blades 10, 12 can also be attached to the handles 20, 22 in any other way, such as by a clamp, hinge, screw or the like. The first and second blades 10, 12 project at an angle of approximately 70 degrees from the handles 20, 22 so the handles 20, 22 do not crowd the field of view of a surgeon, but it is also within the scope of the invention for the blades 10, 12 to project linearly from the handles 20, 22 or at any other angle including a variable angle. In this embodiment, the first and second blades 10, 12 are outwardly curved and have flared openings 50, 52 adjacent to the handles 20, 22. Hooks 60, 62 are fixed on the first and second handles 20, 22 and partially surround the third handle 24, although any other suitable blade design may be used.

The third and fourth handles 24, 26 of the exemplary embodiment are connected to a connecting rod 70 and have hinges 72, 74 to vary the angle of the third and fourth blades 14, 16. The connecting rod 70 can be supported by the stabilizing arm 40. The distance 76 between the third and fourth handles 24, 26 can be changed by sliding the third handle 24 toward or away from the fourth handle 26 on the connecting rod 70 and locking it in place with a lock 78.

The third blade 14 is connected by a movable clamp 80 to the third handle 24 and projects parallel to and between the first and second blades 10, 12. The third blade 14 and the movable clamp 80 can slide along the third handle 24 and be locked into place at multiple locations along the handle 24. The fourth blade 16 is rotatably connected to the fourth handle 26 by a screw 82 or the like and projects parallel to and between the first and second blades 20, 22 and opposite the third blade 24. Fiducials (not shown) may also be added to areas on the speculum, such as movable clamp 80, screw 82, and/or the flared openings 50, 52, to be used as reference points in image-guided surgery.

This embodiment may dilate a small surgical opening (not shown) to 1.5 inches in both directions, allowing a surgeon to adjust the size and shape of the opening to provide suitable illumination, viewing angle and operating leverage at the area of interest. Because of the potentially large dilation capability, this speculum system embodiment can also be used with a microscope, endoscope, or the like.

Also possible with this embodiment is a posterolateral approach to the spine. Two of the blades can be inserted and brought apart to dilate the space between two groups of muscles. Then, the other two blades can be inserted between the first two blades, coupled to them and dilated. This approach can limit the damage to the back muscles caused by spinal surgery and greatly reduce the time needed to recover.

Figure 2:
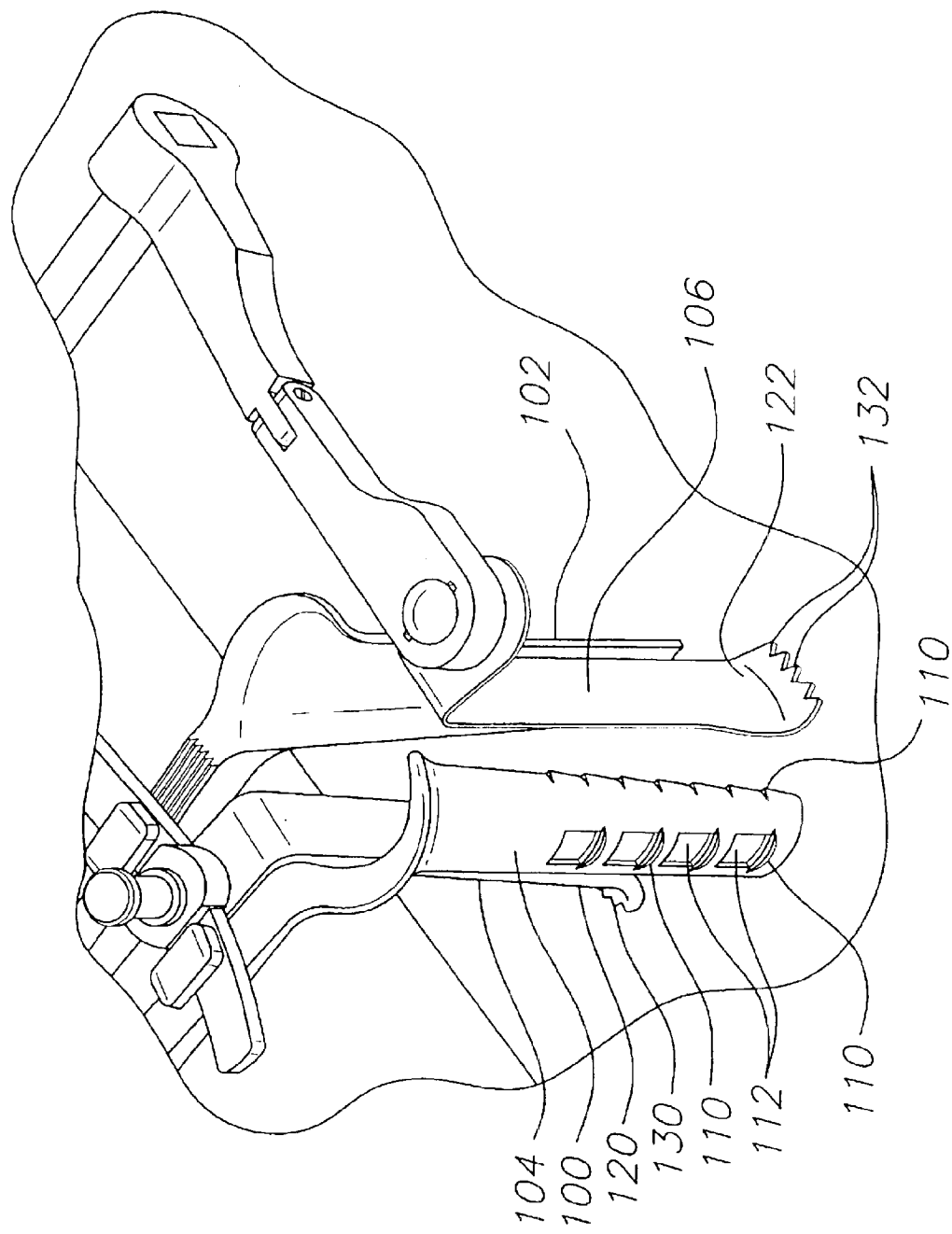
FIG. 2 is a side perspective view of the blades of the embodiment shown in FIG. 1.

Regarding the embodiment shown in FIG. 2, the first and second blades 100, 102 include texture such as ribs 110 or barbs along their outer surfaces. The first and second blades 100, 102 also include openings 112. These ribs 110 and openings 112 can grip onto muscle fiber (not shown), or the like, to counter the body's natural extrusion and hold the blades 100, 102, 104, 106 within a surgical opening. Because these ribs 110 and openings 112 allow the speculum system to grip onto muscle fiber, it can be used for many medical purposes in addition to spinal surgery. For example, a biopsy of a bone tumor on a thigh bone could be completed percutaneously with this speculum system and the tumor can be taken out in minimally invasive surgery. The speculum system could also be used, for example, in ear, nose and throat surgery, obstetrics/gynecology, general surgery, orthopedics, etc.

The blade ends 120, 122 on the outer surfaces of the third and fourth blades 104, 106 flare outward. The blade ends 120, 122 also include teeth 130, 132 for gripping onto muscle fiber or the like to keep the blades 100, 102, 104, 106 sufficiently deep, allowing an appropriate surgical view.

Figure 3:
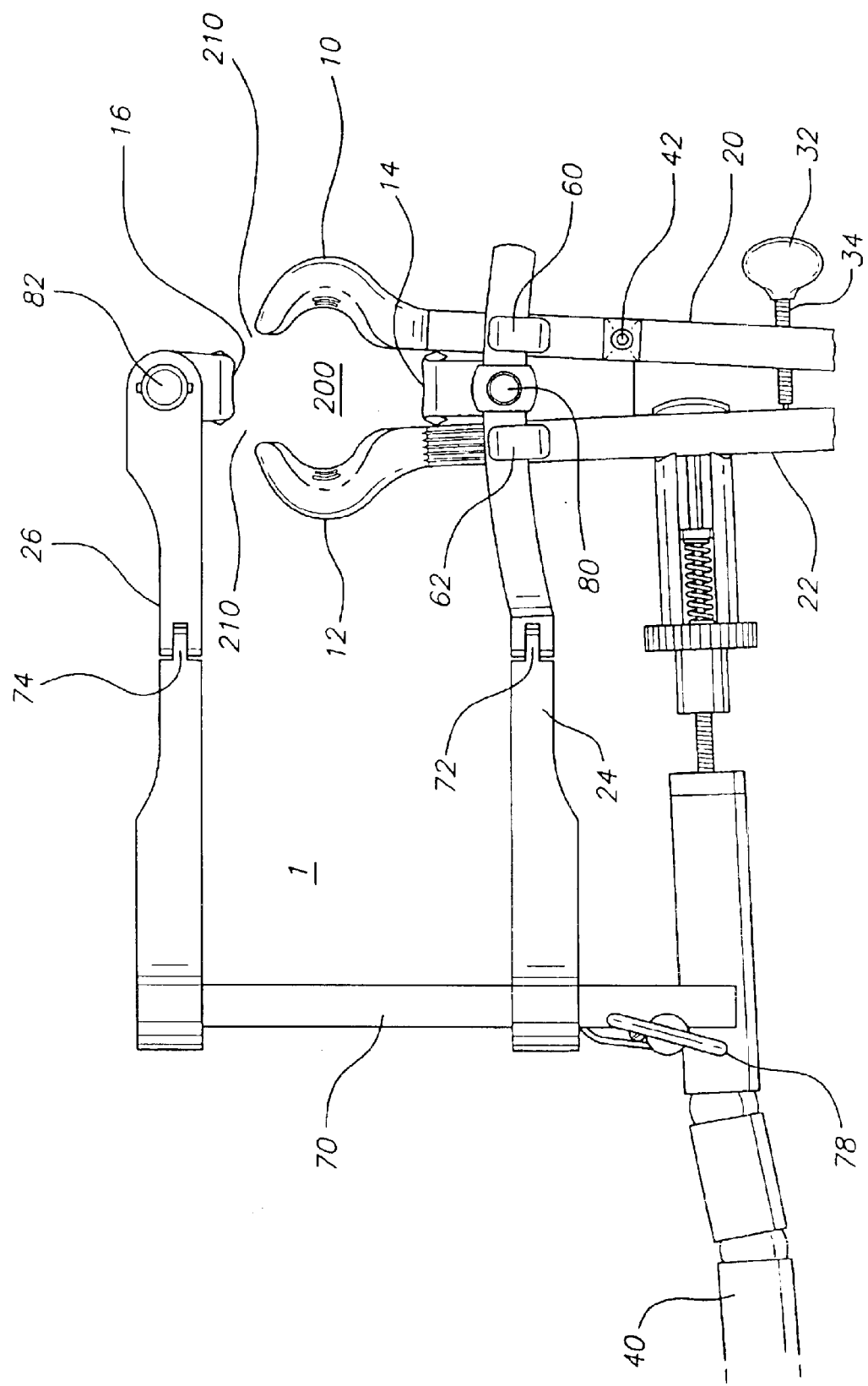
FIG. 3 is a plan view of another exemplary embodiment of the speculum system according to the invention.

A plan view of the above-described embodiment is shown in more detail in FIG. 3. As discussed, the field of view 200, defined as the viewable area between the inner surfaces of the blades 10, 12, 14, 16, can be widened by adjusting the screw 32 between the first and second handles 20, 22 or by sliding the fourth handle 26 away from the third handle 24 on the connecting rod 70. The fourth blade 16 can also be rotated about the axis of the screw 82 to extend the field of view 200. The angle of the field of view 200 can also be adjusted by loosening the stabilizing arm 40, bending the third and fourth handles 24, 26 at their hinges 72, 74, and reconnecting the stabilizing arm 40 to the second handle 22. This embodiment also includes spaces 210 between adjacent blades that allow access to the exposed bodily cavity (not shown) for surgical tools. These spaces can also securely hold cottonoids, which can be tucked behind the blades for safety, security and protection.

The blades 10–16, 102–108 can be made from a substantially nonreflective metal. This is possible because the field of view 200 in this speculum system can be large enough to allow ambient light to illuminate the surgical cavity, so reflection of the light off of the speculum blades is largely unnecessary. The blades 10–16, 102–108 can also be made of a radiolucent material, such as carbon fiber or titanium, to allow the speculum system 1 to be used with fluoroscopy.

Although specific embodiments are disclosed herein, it is expected that persons skilled in the art can and will design alternate instruments and methods that are within the scope of the following claims either literally or under the Doctrine of Equivalents.

What is claimed is:

1. A surgical speculum system comprising:
    a first blade having an inner surface and an outer surface, the first blade coupled to a first handle;
    a second blade having an inner surface and an outer surface, the second blade coupled to a second handle, wherein the first handle is coupled to the second handle such that the inner surface of the first blade faces the inner surface of the second blade;
    a third blade having an inner surface and an outer surface, the third blade coupled to a third handle;
    a fourth blade having an inner surface and an outer surface, the fourth blade coupled to a fourth handle, wherein the third handle is coupled to the fourth handle such that the inner surface of the third blade faces the inner surface of the fourth blade; and
    at least one fiducial coupled to at least one blade,
    wherein at least one of the third handle and fourth handle is coupled to at least one of the first handle and the second handle.

2. The surgical speculum system of claim 1, wherein at least one of the handles is coupled to at least one of the blades at an angle.

3. The surgical speculum system of claim 1, wherein the first handle and the second handle are coupled such that a space between the first blade and the second blade is changeable.

4. The surgical speculum system of claim 3, wherein the third handle and the fourth handle are coupled such that a space between the third blade and the fourth blade is changeable.

5. The surgical speculum system of claim 4, wherein the third and fourth handles are couplable such that the space between the third and fourth blades can be around 1.5 inches.

6. The surgical speculum system of claim 3, wherein the first and second handles are couplable such that the space between the first and second blades can be around 1.5 inches.

7. The surgical speculum system of claim 1, wherein at least one of the blades is convex along a width of its outer surface.

8. The surgical speculum system of claim 1, wherein the outer surface of at least one blade is textured to provide friction.

9. The surgical speculum system of claim 8, wherein the texture includes a rib.

10. The surgical speculum system of claim 1, further comprising teeth on a free end of at least one blade, the teeth projecting at least partially away from the inner surface.

11. The surgical speculum system of claim 1, wherein the first blade is adjacent to the third and fourth blades, and the second blade is adjacent to the third and fourth blades, and wherein the adjacent blades are spaced such that a surgical instrument can be inserted between the adjacent blades.

12. The surgical speculum system of claim 1, wherein at least one inner surface is substantially non-reflective.

13. The surgical speculum system of claim 1, further comprising a stabilizer coupled to at least one of the handles to substantially stabilize movement of the speculum.

14. The surgical speculum system of claim 13, further comprising a stabilizing object coupled to the stabilizer.

15. The surgical speculum system of claim 14, wherein the stabilizing object is a table and the stabilizer includes flexible linkage.

16. The surgical speculum system of claim 1, wherein at least one blade has a length sufficient to reach from a surgical incision to a location of operation.

17. The surgical speculum system of claim 1, further comprising an attachment post coupled to at least one handle for attaching at least one instrument.

18. The surgical speculum system of claim 1, wherein at least one blade comprises an at least partially radiolucent material.

19. The surgical speculum system of claim 1, wherein at least one blade includes an opening on its inner surface.

20. The surgical speculum system of claim 1, wherein the coupler is configured such that the at least one of the third handle and fourth handle can be uncoupled from the at least one of the first handle and second handle.

21. The surgical speculum system of claim 1, wherein the first handle and the second handle curve upward.

* * * * *